United States Patent [19]

Krämer et al.

[11] Patent Number: 4,985,421
[45] Date of Patent: Jan. 15, 1991

[54] FUNGICIDAL SUBSTITUTED DIOXOLANYLETHYLAMINE

[75] Inventors: Wolfgang Krämer, Burscheid; Joachim Weissmüller, Monheim; Dieter Berg, Wuppertal; Wilhelm Brandes, Leichlingen; Stefan Dutzmann, Duesseldorf, all of Fed. Rep. of Germany

[73] Assignee: Bayer Aktiengesellschaft, Leverkusen, Fed. Rep. of Germany

[21] Appl. No.: 395,231

[22] Filed: Aug. 17, 1989

[30] Foreign Application Priority Data

Aug. 23, 1988 [DE] Fed. Rep. of Germany ....... 3828490

[51] Int. Cl.$^5$ ................. C01D 285/00; C01D 491/00; C01D 273/00; C01D 211/00
[52] U.S. Cl. .................................. 514/212; 514/227.8; 514/233.8; 514/321; 514/422; 514/462; 540/543; 544/6; 544/70; 548/407; 549/341; 546/15
[58] Field of Search ............ 514/422, 462, 212, 227.8, 514/233.8, 321; 540/609, 543; 544/61, 153, 70, 6; 546/187, 15; 548/526, 407; 549/341

[56] References Cited

U.S. PATENT DOCUMENTS 4,851,405  7/1989  Kramer et al. ...................... 549/341

FOREIGN PATENT DOCUMENTS 0097822  1/1984  European Pat. Off. ............ 514/122
0131793  1/1985  European Pat. Off. .
0281842  9/1988  European Pat. Off. .
1965321  9/1970  Fed. Rep. of Germany .

OTHER PUBLICATIONS

Chemical and Pharmaceutical Bulletin, vol. 32, No. 3 (1984), pp. 967–976, "Studies on . . . 4-ylmethyl)piperidines".

Primary Examiner—Mukund J. Shah
Assistant Examiner—Edward C. Ward
Attorney, Agent, or Firm—Sprung Horn Kramer & Woods

[57] ABSTRACT

Fungicidal substituted dioxolanylethylamine of the formula

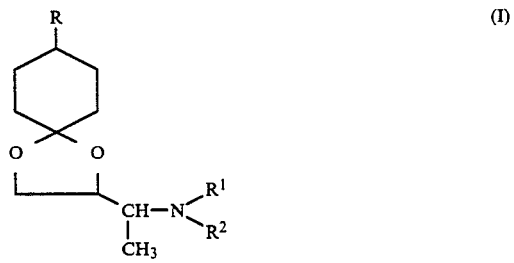

in which
  R represents alkyl, or represents in each case optionally substituted cycloalkylalkyl, aralkyl, cycloalkyl or aryl, and
  $R^1$ and $R^2$ independently of one another each represents hydrogen, alkyl, alkenyl, alkinyl, alkoxyalkyl, dialkoxyalkyl, hydroxyalkyl, hydroxyalkoxyalkyl, alkoxycarbonylalkyl, dioxolanylalkyl, dioxanylalkyl or oxolanylalkyl, or represents in each case optionally substituted cycloalkylalkyl, cycloalkyl, aralkyl, aralkenyl or aryl, or
  $R^1$ and $R^2$, together with the nitrogen atom to which they are bonded, represent an optionally substituted saturated heterocyclic radical, which can optionally contain further hetero atoms,
and acid addition salts thereof.

Intermediates wherein the amino group is an electron-withdrawing leaving group are also new.

11 Claims, No Drawings

FUNGICIDAL SUBSTITUTED DIOXOLANYLETHYLAMINE

The invention relates to new substituted dioxolanylethylamines, several processes for their preparation, their use in agents for combating pests and new intermediate products.

It is known that certain aminomethyldioxolanes, such as, for example, the compound 2-isobutyl-2-methyl-4-(1-piperidinylmethyl)-1,3-dioxolane or the compound 2-methyl-2-nonyl-4-di-n-butylaminomethyl-1,3-dioxolane or the compound 2-(2-cyclohexylmethyl-2-propyl)-2-methyl-4-(1-piperidinylmethyl)-1,3-dioxolane or the compound 2-(2-cyclohexylmethyl-2-propyl)-2-methyl-4-(1-perhydroazepinyl-methyl)-1,3-dioxolane, have fungicidal properties (compare, for example, EP 97,822).

However, the activity of these already known compounds is not completely satisfactory in all fields of use, especially when low amounts are applied and in the case of low concentrations.

New substituted dioxolanylethylamines of the general formula (I)

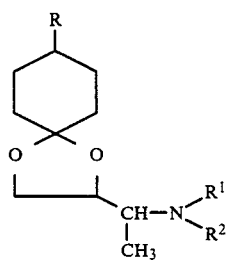

in which
R represents alkyl, or represents in each case optionally substituted cycloalkylalkyl, aralkyl, cycloalkyl or aryl, and
$R^1$ and $R^2$ independently of one another each represents hydrogen, alkyl, alkenyl, alkinyl, alkoxyalkyl, dialkoxyalkyl, hydroxyalkyl, hydroxyalkoxyalkyl, alkoxycarbonylalkyl, dioxolanylalkyl, dioxanylalkyl or oxolanylalkyl, or represents in each case optionally substituted cycloalkylalkyl, cycloalkyl, aralkyl, aralkenyl or aryl, or
$R^1$ and $R^2$, together with the nitrogen atom to which they are bonded, represent an optionally substituted saturated heterocyclic radical, which can optionally contain further hetero atoms,
and acid addition salts therefor have been found.

The compounds of the formula (I) can exist as geometric and/or optical isomers or isomer mixtures of varying composition. Both the pure isomers and the isomer mixtures are claimed according to the invention. "Compounds of the formula (I)" as employed herein means all forms.

It has furthermore been found that the new substituted dioxolanylethylamines of the general formula (I)

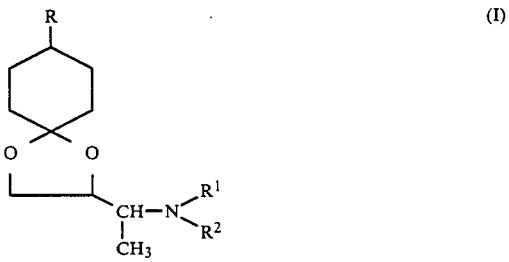

in which
R represents alkyl, or represents in each case optionally substituted cycloalkylalkyl, aralkyl, cycloalkyl or aryl, and
$R^1$ and $R^2$ independently of one another each represents hydrogen, alkyl, alkenyl, alkinyl, alkoxyalkyl, dialkoxyalkyl, hydroxyalkyl, hydroxyalkoxyalkyl, alkoxycarbonylalkyl, dioxolanylalkyl, dioxanylalkyl or oxolanylalkyl, or represents in each case optionally substituted cycloalkylalkyl, cycloalkyl, aralkyl, aralkenyl or aryl, or
$R^1$ and $R^2$, together with the nitrogen atom to which they are bonded, represent an optionally substituted saturated heterocyclic radical, which can optionally contain further hetero atoms,
and acid addition salts thereof, are obtained by a process in which
(a) substituted dioxolanes of the formula (II)

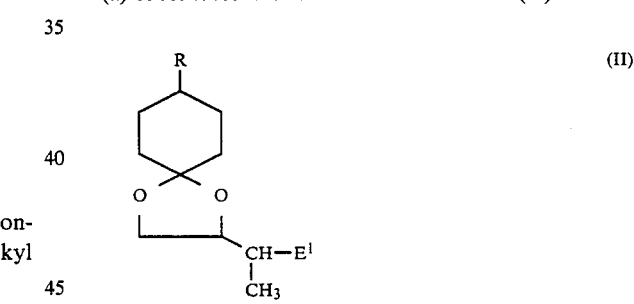

in which
R has the abovementioned meaning and
$E^1$ represents an electron-withdrawing leaving group,
are reacted with amines of the formula (III)

in which
$R^1$ and $R^2$ have the abovementioned meanings, if appropriate in the presence of a diluent and if appropriate in the presence of an acid-binding agent, or by a process in which
(b) the substituted dioxolanylethylamines according to the invention, which are obtainable by process (a), of the formula (Ia)

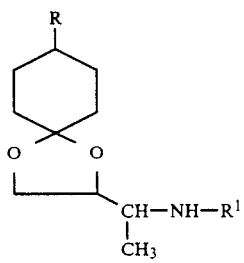

in which

R and R¹ have the abovementioned meanings, are reacted with alkylating agents of the formula (IV)

$$R^{2\text{-}1}\text{-}E^2 \quad (IV)$$

in which

R²⁻¹ represents alkyl, alkenyl, alkinyl, alkoxyalkyl, dialkoxyalkyl, hydroxyalkyl, hydroxyalkoxyalkyl, alkoxycarbonylalkyl, dioxolanylalkyl, dioxanylalkyl or oxolanylalkyl, or represents in each case optionally substituted cycloalkylalkyl, cycloalkyl, aralkyl or aralkenyl and E² represents an electron-withdrawing leaving group, if appropriate in the presence of a diluent and if appropriate in the presence of an acid-binding agent, and if appropriate an acid is then added on or the process is followed by a physical resolution method.

Finally, it has been found that the new substituted dioxolanylethylamines of the general formula (I) have an action against pests, in particular against fungal pests.

Surprisingly, the substituted dioxolanylethylamines of the general formula (I) according to the invention exhibit a better fungicidal activity than the aminomethyldioxolanes known from the prior art, such as, for example, the compound 2-isobutyl-2-methyl-4-(1-piperidinylmethyl)-1,3-dioxolane or the compound 2-methyl-2-nonyl-4-di-n-butyl-aminomethyl-1,3-dioxolane or the compound 2-(2-cyclohexyl- methyl-2-propyl)-2methyl-4-(1-piperidinylmethyl)-1,3-dioxolane or the compound 2-(2-cyclohexylmethyl-2-propyl)-2-methyl-4-(1-perhydroazepinylmethyl)-1,3-dioxolane, which are closely related compounds chemically and from the point of view of their action.

Formula (I) provides a general definition of the substituted dioxolanylethylamines according to the invention. Preferred compounds of the formula (I) are those in which R represents straight-chain or branched alkyl having 1 to 12 carbon atoms, or represents cycloalkylalkyl or cycloalkyl having in each case 3 to 7 carbon atoms in the cycloalkyl part and if appropriate 1 to 6 carbon atoms in the straight-chain or branched alkyl part and in each case optionally substituted by one or more identical or different substituents from the group comprising halogen and/or straight-chain or branched alkyl having 1 to 8 carbon atoms, or represents aralkyl or aryl having in each case 6 to 10 carbon atoms in the aryl part-and if appropriate 1 to 6 carbon atoms in the straight-chain or branched alkyl part and in each case optionally substituted by one or more identical or different substituents from the group comprising halogen and/or straight-chain or branched alkyl having 1 to 8 carbon atoms, and R¹ and R² independently of one another each represents hydrogen, or represents in each case straight-chain or branched alkyl having 1 to 12 carbon atoms, alkenyl having 3 to 8 carbon atoms, alkinyl having 3 to 8 carbon atoms, hydroxyalkyl having 2 to 6 carbon atoms, alkoxyalkyl or dialkoxyalkyl having in each case 1 to 6 carbon atoms or hydroxyalkoxyalkyl having 2 to 6 carbon atoms in the individual alkyl parts, or represent alkoxycarbonylalkyl having 1 to 6 carbon atoms per alkoxy and alkyl part, or represents in each case straight-chain or branched dioxolanylalkyl, dioxanylalkyl or oxolanylalkyl having in each case 1 to 4 carbon atoms in the alkyl part, or represent cycloalkyl or cycloalkylalkyl having in each case 3 to 7 carbon atoms in the cycloalkyl part and if appropriate 1 to 4 carbon atoms in the straight-chain or branched alkyl part and in each case optionally substituted in the cycloalkyl part by one or more identical or different substituents, possible substituents in each case being: halogen, and in each case straight-chain or branched alkyl, alkoxy, halogenoalkyl or halogenoalkoxy having in each case 1 to 4 carbon atoms and if appropriate 1 to 9 identical or different halogen atoms; or furthermore represents arylalkyl, arylalkenyl or aryl having in each case 6 to 10 carbon atoms in the aryl part and if appropriate up to 6 carbon atoms in the straight-chain or branched alkyl or alkenyl part and in each case optionally substituted in the aryl part by one or more identical or different substituents, possible substituents on the aryl in each case being: halogen, cyano, nitro and in each case straightchain or branched alkyl, alkoxy, alkylthio, halogenoalkyl, halogenoalkoxy, halogenoalkylthio, alkoxycarbonyl or alkoximinoalkyl having in each case 1 to 4 carbon atoms in the individual alkyl parts and if appropriate 1 to 9 identical or different halogen atoms, or R¹ and R², together with the nitrogen atom to which they are bonded, represent a saturated 5- to 7-membered heterocyclic radical which is optionally substituted by one or more identical or different substituents and can optionally contain a further hetero atom, in particular nitrogen, oxygen or sulphur, possible substituents being: in each case straight-chain or branched alkyl or hydroxyalkyl having in each case 1 to 4 carbon atoms.

Particularly preferred compounds of the formula (I) are those in which

R represents straight-chain or branched alkyl having 1 to 8 carbon atoms, or represents cyclohexyl which is optionally substituted by one to three identical or different substituents from the group comprising chlorine, methyl, ethyl, n- or i-propyl and n-, i-, s- or t- butyl, or represents cyclohexylalkyl having 1 to 4 carbon atoms in the straight-chain or branched alkyl part and optionally substituted in the cyclohexyl part by one to three identical or different substituents from the group comprising chlorine, methyl, ethyl, n-or i-propyl and n-, i-, s- or t-butyl, or represents phenyl which is optionally substituted by one to three identical or different substituents from the group comprising fluorine, chlorine, bromine, methyl, ethyl, n- or i-propyl, n-, i-, s- or t-butyl, or represents phenylalkyl having 1 to 4 carbon atoms in the straight-chain or branched alkyl part and optionally substituted in the phenyl part by one to three identical or different substituents from the group comprising fluorine, chlorine, bromine, methyl, ethyl, n- or i-propyl and n-, i-, s- or t-butyl, and R¹ and R² independently of one another each represents hydrogen, methyl, ethyl, n- or i-propyl, n-, i-, s- or t-butyl, n- or i-pentyl, n- or i-hexyl, n-or i-heptyl, n- or i-octyl, allyl, n- or ibutenyl, n- or i-pentenyl,. propargyl, n- or ibutinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, dioxanylethyl, oxolanylmethyl or oxolanylethyl, or represent cyclopropyl, cyclopropylmethyl, cyclopropylethyl, cyclopropylpropyl, cyclopentyl, cyclopentylmethyl, cyclohexyl or cyclohexylmethyl, in each case optionally substituted by one to five identical or different substituents from the group comprising fluorine, chlorine, bromine, methyl, ethyl, n- or i-propyl, n-, i-, s- or t-butyl, trifluoromethyl or trifluoromethoxy, or represent phenyl, benzyl or phenylethyl, in each case optionally substituted by one to three identical or different substituents, possible substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl or methoximinomethyl, or R¹ and R², together with the nitrogen atom to which they are bonded, represent a heterocyclic radical of the formula

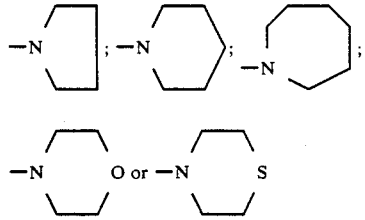

which is optionally substituted by one to three identical or different substituents, possible substituents in each case being: methyl, ethyl or hydroxymethyl.

Especially preferred compounds of the formula (I) are those in which

R represents cyclohexyl or phenyl, or represents one of the radicals

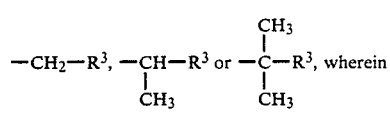

R³ in each case represents hydrogen, methyl, ethyl, n- or i-propyl, n-, i-, s- or t-butyl, neopentyl, cyclohexyl or phenyl, and R¹ and R² independently of one another each represents hydrogen, methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, oxolanylmethyl, oxolanylethyl, cyclopropylmethyl, dichlorocyclopropylmethyl, dimethylcyclopropylmethyl, dichlorodimethylcyclopropylmethyl, cyclopentyl, cyclohexyl or cyclohexylmethyl, or R¹ and R², together with the nitrogen atom to which they are bonded, represent a heterocyclic radical of the formula

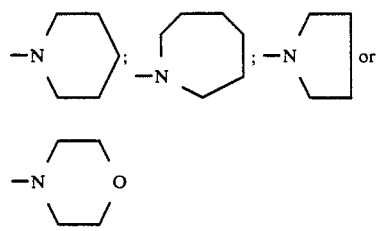

which is optionally substituted by one to three identical or different substituents, possible substituents in each case being: methyl, ethyl or hydroxymethyl.

Preferred compounds according to the invention are also addition products of acids and those substituted dioxolanylethylamines of the formula (I) in which the substituents R, R¹ and R² have the meanings which have already been mentioned for these substituents.

The acids which can be added on and which lead to addition products which are tolerated by plants include, preferably, hydrogen halide acids, such as, for example, hydrochloric acid and hydrobromic acid, in particular hydrochloric acid, and furthermore phosphoric acid, nitric acid, mono-, bi- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, sulphonic acids, such as p-toluenesulphonic acid and 1,5-naphthalenedisulphonic acid, as well as saccharin or thiosaccharin.

If, for example, 8-t-butyl-2-(1-chloroethyl)-1,4-dioxaspiro[4,5]decane and piperidine are used as starting substance, the course of the reaction in process (a) according to the invention can be represented by the following equation:

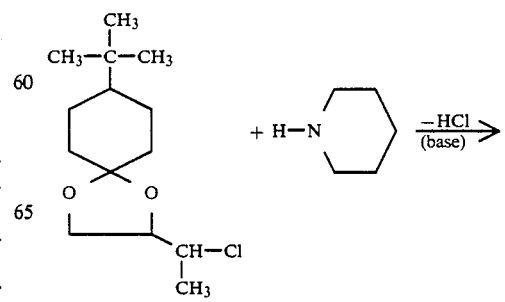

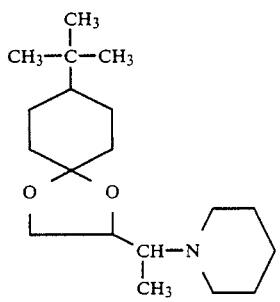

If, for example, 8-t-butyl-2-(1-methylamino)-ethyl-1,4-dioxaspiro[4,5]decane and allyl bromide are used as starting substances, the course of the reaction of process (b) according to the invention can be represented by the following equation:

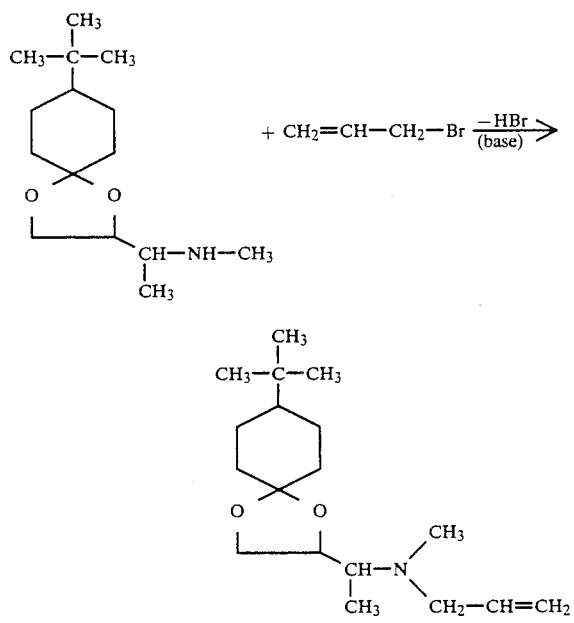

Formula (II) provides a general definition of the substituted dioxolanes required as starting substances for carrying out process (a) according to the invention. In this formula (II), R preferably represents those radicals which have already been mentioned for this substituent in connection with the description of the substances of the formula (I) according to the invention.

$E^1$ preferably represents halogen, in particular iodine, chlorine or bromine, or represents alkylsulphonyloxy which is optionally substituted by halogen, such as fluorine, chlorine, bromine or iodine, or represents arylsulphonyloxy which is optionally substituted by alkyl having 1 to 4 carbon atoms, such as, for example, methanesulphonyloxy, trifluoromethanesulphonyloxy or p-toluenesulphonyloxy.

The substituted dioxolanes of the formula (II) are not yet known and the invention likewise relates to them. They are obtained by processes analogous to known processes (compare, for example, Liebigs Ann. Chem. 1984, 1298–1301; Z. Naturforsch. B, Anorg. Chem., Org. Chem. 4013, 393–397 [1985] or J. Org. Chem. 51, 1894–1897 [1986] and the preparation examples), for example by a procedure in which cyclohexanone derivatives of the formula (V)

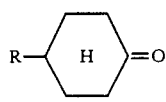

in which
R has the abovementioned meaning,
either
(a) are cyclized with alcohols of the formula (VIa)

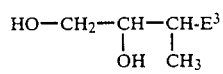

in which
$E^3$ represents halogen or hydroxyl, if appropriate in the presence of a diluent, such as, for example, toluene, and if appropriate in the presence of an acid catalyst, such as, for example, p-toluenesulphonic acid, at temperatures between 40° C. and 150° C., or
(b) are reacted with oxiranyl compounds of the formula (VIb)

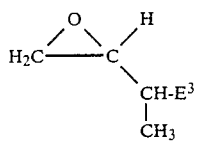

in which
$E^3$ represents halogen or hydroxyl, if appropriate in the presence of a diluent, such as, for example, carbon tetrachloride, and if appropriate in the presence of a catalyst, such as, for example, tin tetrachloride, at temperatures between −20° C. and +40° C., and if appropriate in the cases where $E^3$ in formula (VIa) or (VIb) represents a hydroxyl group, the hydroxymethyldioxolanes thus obtainable, of the formula (VII)

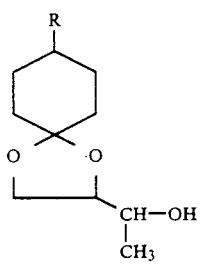

in which
R has the abovementioned meaning, are reacted in a second stage with optionally substituted alkyl- or arylsulphonyl halides of the formula (VIII)

Z-SO₂-Hal    (VIII)

in which
Hal represents halogen, in particular chlorine, and
Z represents alkyl, in each case optionally substituted by halogen, such as fluorine, chlorine, bromine or iodine, or represents aryl which is optionally substituted by alkyl having 1 to 4 carbon atoms, such as, in particular, methyl, trifluoromethyl or 4-methylphenyl, if appropriate in the presence of a diluent, such as, for example, diethyl ether, and if appropriate in the presence of an acid-binding agent, such as, for example, pyridine or triethylamine, at temperatures between −20° C. and +100° C.

The geometric isomers and diastereomers thereby obtainable can either be further reacted as mixtures in process (a) according to the invention or resolved by customary resolution methods (chromatography or crystallization).

The cyclohexanone derivatives of the formula (V) are known or can be prepared by processes analogous to known processes (compare, for example, Tetrahedron Letters 28, 2347–2350 [1987]; Tetrahedron Lett. 27, 2875–2878 [1986]; Tetrahedron Lett. 1979, 3209–3212; J. Am. chem. Soc. 109, 6887–6889 [1987]; J. Am. chem. Soc. 95, 3646–3651 [1973]; J. Am. chem. Soc. 94, 7599–7600 [1972]; Bull. chem. Soc. Jap. 60, 1721–1726 [1987]; Chem. Lett. 1986, 1593–1596; Synth. Commun. 15, 759–764 [1985]; Synth. Commun. 12, 267–277 [1982]; J. chem. Soc.; Chem. Commun. 1984, 762–763; J. org. Chem. 38, 1775–1776 [1973]; U.S. Pat. No. 4,251,398; 3,960,961; EP 2,136; DE 2,636,684; DE 2, 509,183; FR 2,231,650 and the preparation examples).

The alcohols of the formula (VIa) are likewise known (compare, for example, EP 200,267; DE- 2,937,840; U.S. Pat. No. 4,035,178; Tetrahedron 27, 3197–3205 [1971]; Tetrahedron 35, 2583–2589 [1979]; Carbohydrate Res. 31, 17–26 [1973]).

The oxiranyl compounds of the formula (VIb) are likewise known (compare, for example, EP 3,664; J.Am. chem. Soc. 96, 5254–5255 [1974]; Tetrahedron Lett. 1977, 4397–4400; Tetrahedron Lett. 1979, 4733–4736; and Tetrahedron Lett. 21. 4843–4846 [1980]).

The sulphonyl halides of the formula (VIII) are generally known compounds of organic chemistry.

Formula (III) provides a general definition of the amines furthermore required as starting substances for carrying out process (a) according to the invention. In this formula (III), $R^1$ and $R^2$ preferably represent those radicals which have already been mentioned for these substituents in connection with the description of the substances of the formula (I) according to the invention.

The amines of the formula (III) are generally known compounds of organic chemistry.

Formula (Ia) provides a general definition of the substituted dioxolanylethylamines required as starting substances for carrying out process (b) according to the invention. In this formula (Ia), R and $R^1$ preferably represent those radicals which have already been mentioned for these substituents in connection with the description of the substances of the formula (I) according to the invention.

The substituted dioxolanxylethylamines of the formula (Ia) are compounds according to the invention and are obtainable with the aid of process (a) according to the invention.

Formula (IV) provides a general definition of the alkylating agents furthermore required as starting substances for carrying out process (b) according to the invention. In this formula (IV), $R^{2-1}$ preferably represents in each case straight-chain or branched alkyl having 1 to 12 carbon atoms, alkenyl having 3 to 8 carbon atoms, alkinyl having 3 to 8 carbon atoms hydroxyalkyl having 2 to 6 carbon atoms, alkoxyalkyl or dialkoxyalkyl having 1 to 6 carbon atoms or hydroxyalkoxyalkyl having 2 to 6 carbon atoms in the individual alkyl parts, or represents alkoxycarbonylalkyl having 1 to 6 carbon atoms per alkoxy and alkyl part, or represents in each case straight-chain or branched dioxolanylalkyl, dioxanylalkyl or oxolanylalkyl having in each case 1 to 4 carbon atoms in the alkyl part, or represents cycloalkyl or cycloalkylalkyl having in each case 3 to 7 carbon atoms in the cycloalkyl part and if appropriate 1 to 4 carbon atoms in the straight-chain or branched alkyl part and in each case optionally substituted in the cycloalkyl part by one or more identical or different substituents, possible substituents in each case being: halogen and in each case straight-chain or branched alkyl, alkoxy, halogenoalkyl or halogenoalkoxy having in each case 1 to 4 carbon atoms and if appropriate 1 to 9 identical or different halogen atoms; or furthermore represents arylalkyl or arylalkenyl having in each case 6 to 10 carbon atoms in the aryl part and up to 6 carbon atoms in the straight-chain or branched alkyl or alkenyl part and in each case optionally substituted in the aryl part by one or more identical or different substituents, possible substituents on the aryl in each case being: halogen, cyano, nitro and in each case straight-chain or branched alkyl, alkoxy, alkylthio, halogenoalkyl, halogenoalkoxy, halogenoalkylthio, alkoxycarbonyl or alkoximinoalkyl having in each case 1 to 4 carbon atoms in the individual alkyl parts and if appropriate 1 to 9 identical or different halogen atoms.

$R^{2-1}$ particularly preferably represents methyl, ethyl, n-or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, dioxolanylmethyl, dioxolanylethyl, dioxanylmethyl, dioxanylethyl, oxolanylmethyl or oxolanylethyl, or cyclopropyl, cyclopropylmethyl, cyclopropylethyl, cyclopropylpropyl, cyclopentyl, cyclopentylmethyl, cyclohexyl or cyclohexylmethyl, in each case optionally substituted by one to five identical or different substituents from the group comprising fluorine, chlorine, bromire, methyl, ethyl, n- or i-propyl, n-, i-, s- and t-butyl, trifluoromethyl or trifluoromethoxy, or represents benzyl or phenylethyl, in each case optionally substituted by one to three identical or different substituents, possible substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl or methoximinomethyl.

$R^{2-1}$ especially preferably represents methyl, ethyl, n-or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, cyclopropylmethyl, oxolanylmethyl, oxolanylethyl, dichlorocyclopropylmethyl, dimethylcyclopropylmethyl, dichlorodimethylcyclopropylmethyl, cyclopentyl, cyclohexyl or cyclohexylmethyl.

$E^2$ preferably represents halogen, in particular chlorine, bromine or iodine, or represents alkylsulphonyloxy or alkoxysulphonyloxy having in each case 1 to 4 carbon atoms and in each case optionally substituted by halogen, such as fluorine, chlorine, bromine or iodine, or represents arylsulphonyloxy which is optionally substituted by alkyl having 1 to 4 carbon atoms, such as, for example, methane-sulphonyloxy, methoxysulphonyloxy or p-toluene-sulphonyloxy.

The alkylating agents of the formula (IV) are likewise generally known compounds of organic chemistry or are obtainable by processes analogous to generally known processes.

Possible diluents for carrying out processes (a) and (b) according to the invention are inert organic solvents or aqueous systems. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide; esters, such as ethyl acetate; sulphoxides, such as dimethyl sulphoxide, or alcohols, such as methanol, ethanol or propanol.

If appropriate, processes (a) and (b) according to the invention can also be carried out in a two-phase system, such as, for example, water/toluene or water/methylene chloride, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}/C_{15}$-alkylammonium chloride, dibenzyldimethyl-ammonium methylsulphate, dimethyl-$C_{12}/C_{14}$-alkylbenzylammonium chloride, tetrabutylammonium hydroxide, 15-crown-5, 18-crown-6, triethylbenzylammonium chloride or trimethylbenzylammonium chloride. It is also possible for processes (a) and (b) according to the invention to be carried out without addition of a solvent.

Possible acid-binding agents for carrying out processes (a) and (b) according to the invention are all the inorganic and organic bases which can usually be employed. Bases which are preferably used are alkali metal hydroxides, alcoholates, carbonates or bicarbonates, such as, for example, sodium hydroxide, sodium methylate, sodium ethylate, sodium carbonate or sodium bicarbonate, or also tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

It is also possible for the amines of the formulae (III) and (Ia) used as reaction participants to be simultaneously employed as the acid-binding agent in a corresponding excess.

The reaction temperatures can be varied within a substantial range in carrying out processes (a) and (b) according to the invention. The reaction is in general carried out at temperatures between $+20°$ C. and $+200°$ C., preferably at temperatures between $80°$ C. and $+180°$ C.

Processes (a) and (b) according to the invention are in general carried out under normal pressure. However, it is also possible for the processes to be carried out under increased pressure in the range between 1 and 20 bar. The procedure under increased pressure is particularly advisable if one or more of the reaction participants is in gaseous form under normal pressure and at the required reaction temperature.

For carrying out process (a) according to the invention, in general 1.0 to 10.0 mols, preferably 1.0 to 5.0 mols, of amine of the formula (III) and if appropriate 1.0 to 10.0 mols, preferably 1.0 to 5.0 mols, of acid-binding agent and if appropriate 0.1 to 1.0 mol of phase transfer catalyst are employed per mol of substituted heterocyclic compound of the formula (II).

For carrying out process (b) according to the invention, in general 1.0 to 5.0 mols, preferably 1.0 to 2.0 mols, of alkylating agent of the formula (IV) and 1.0 to 5.0 mols, preferably 1.0 to 2.0 mols, of acid-binding agent, and if appropriate 0.1 to 1.0 mol of phase transfer catalyst are employed per mol of dioxolanylethylamine of the formula (Ia).

The reaction is carried out and the reaction products of the formula (I) are worked up and isolated by customary methods in both cases.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and they can be isolated in a known manner, for example by filtration, and if appropriate purified by washing with an inert organic solvent.

The active compounds according to the invention display a potent action against pests and can be used in practice for combating undesirable harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form; Drechslera, syn: Helminthosporium); Cochliobolus species, such as, for example, *Cochliobolus*

*sativus* conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success here for combating cereal diseases, such as, for example, against the brown glume of wheat causative organism (*Leptosphaeria nodorum*) or against the leaf spot disease of barley causative organism (*Pyrenophora teres*), or against the leaf spot disease of wheat causative organism (*Cochliobolus sativus*) and against mildew and rust species, or for combating diseases in fruit and vegetable growing, such as, for example, against the apple scab causative organism (*Venturia inaequalis*), or against the cucumber mildew causative organism (*Sphaerotheca fuliginea*), or for combating diseases in rice-growing, such as, for example, against the rice spot disease causative organism (*Pyricularia oryzae*).

The active compounds according to the invention moreover exhibit a good in-vitro activity.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or for dispersing agents, and/or foam-forming agents. In the case of the use of water as an extender, organic solvents for example, can also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, nontmorillonite or diatomaceous earth, and ground synthetic minerals, such as highly-dispersed silicic acid, alumina and silicates; as solid carriers for granules there are suitable: for example crushed and fractionateol natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phosphosipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

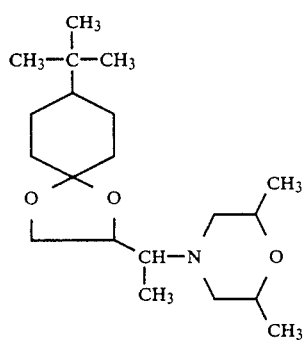

(Process a)

A mixture of 14 g (0.054 mol) of 8-t-butyl-2-(1-chloroethyl)-1,4-dioxaspiro[4,5]decane, 11 g (0.096 mol) of cis-2,6-dimethylmorpholine, 12 g (0.087 mol) of potassium carbonate and 1 g of potassium iodide in 100 ml of ethanol is heated at 180° C. under a pressure of 14 bar for 20 hours. After cooling, the reaction mixture is concentrated, the residue is taken up in methylene chloride, the mixture is washed several times with water, dried over sodium sulphate and concentrated in vacuo and the residue is chromatographed over silica gel using petroleum ether/ethyl acetate (10 : 1).

2.2 g of an isomer (I) with the $^1$H-NMR data:δ(ppm): 4.0–4.15 (m, 2H), 3.75–3.85 (m,1H) and 1.1 (d,3H) and 1.2 g of an isomer (II) of refractive index 1.4745 of 8-t-butyl-2-[1-(cis-2,6-dimethyl-4-morpholinyl)-ethyl]-1,4-dioxaspiro[4,5]decane (a total yield of 18.5% of theory) are obtained.

PREPARATION OF THE STARTING COMPOUND

Example II-1

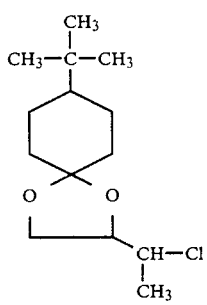

A solution of 15 g (0.057 mol) of tin tetrachloride in 40 ml of carbon tetrachloride is added dropwise to a solution of 38.2 g (0.36 mol) of 1,2-epoxy-3-chlorobutane and 44 g (0.286 mol) of 4-t-butyl-cyclohexanone in 100 ml of carbon tetrachloride, while stirring, such that the temperature of the reaction mixture does not exceed 32° C. When the addition has ended, the mixture is stirred at room temperature for 4 hours and then diluted with 100 ml of toluene, washed with 200 ml of 10 percent strength sodium hydroxide solution and water in succession and dried over potassium carbonate and sodium sulphate and the solvent is removed in vacuo.

71 g (74% of theory) of 8-t-butyl-2-(1-chloroethyl)-1,4-dioxaspiro[4,5]decane are obtained as an isomer mixture of refractive index $n_D^{20}$ 1.4740.

The following substituted dioxolanylethylamines of the general formula (I) are obtained in a corresponding manner and in accordance with the general instructions on the preparation:

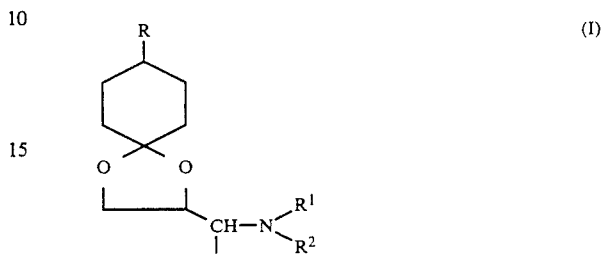

| Ex. No. | R | $-N\genfrac{}{}{0pt}{}{R^1}{R^2}$ | physical properties |
|---|---|---|---|
| 2 | (CH$_3$)$_3$C— | —N(piperidinyl) | $n_D^{20}$ 1.4836 (Isomer I) |
| 3 | (CH$_3$)$_3$C— | —N(cis-2,6-dimethylmorpholinyl) | $n_D^{20}$ 1.4765 (Isomer mixture) |
| 4 | (CH$_3$)$_3$C— | —N(piperidinyl) | $n_D^{20}$ 1.4791 (Isomer II) |
| 5 | (CH$_3$)$_3$C— | —NH—(4-methylcyclohexyl) | $n_D^{20}$ 1.4840 (Isomer I) |
| 6 | (CH$_3$)$_3$C— | —NH—(4-methylcyclohexyl) | $n_D^{20}$ 1.4834 (Isomer II) |
| 7 | (CH$_3$)$_3$C— | —NH—CH$_2$—(cyclohexyl) | $n_D^{20}$ 1.4732 (Isomer I) |
| 8 | (CH$_3$)$_3$C— | —NH—CH$_2$—(3,3,5-trimethylcyclohexyl) | $n_D^{20}$ 1.4796 (Isomer I) |

-continued

| Ex. No. | R | $-N\begin{smallmatrix}R^1\\R^2\end{smallmatrix}$ | physical properties |
|---|---|---|---|
| 9 | $(CH_3)_3C-$ | −NH−CH₂−(3,3,5-trimethylcyclohexyl) | $n_D^{20}$ 1.4765 (Isomer II) |
| 10 | $(CH_3)_3C-$ | −N(3,5-dimethylpiperidinyl) (cis) | ¹H-NMR*: 3.95–4.1 (m,2H) 3.75–3.85 (m,1H) 1.02 (d,3H) |
| 11 | $(CH_3)_3C-$ | $-NH-CH_2-CH(C_2H_5)_2$ | $n_D^{20}$ 1.4716 (Isomer I) |
| 12 | $(CH_3)_3C-$ | $-NH-CH_2(C_2H_5)_2$ | $n_D^{20}$ 1.4683 (Isomer mixture) |
| 13 | $(CH_3)_3C-$ | −N(3,5-dimethylpiperidinyl) (cis) | $n_D^{20}$ 1.4743 (Isomer II) |
| 14 | $(CH_3)C$ | −NH−(2-methylcyclohexyl) | $n_D^{20}$ 1.4810 (Isomer mixture) |
| 15 | $(CH_3)_3C$ | −NH−CH₂−(tetrahydrofuran-2-yl) | $n_D^{20}$ 1.4908 (Isomer mixture) |

*The ²H-NMR spectra were recorded in deuterochloroform (CDCl₃) using tetramethylsilane (TMS) as the internal standard. The chemical shift is stated as the δ value in ppm.

USE EXAMPLES

The compounds shown below were employed as comparison substances in the use examples which follow:

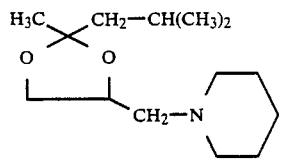

(A)

2-Isobutyl-2-methyl-4-(1-piperidinylmethyl)-1,3-dioxolane

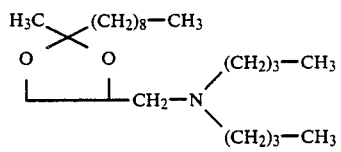

(B)

2-Methyl-2-nonyl-4-di-n-butylaminomethyl-1,3-dioxolane

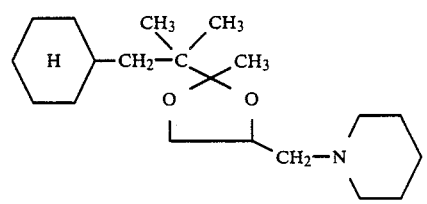

(C)

2-(2-Cyclohexylmethyl-2-propyl)-2-methyl-4-(1-piperidinylmethyl)-1,3-dioxolane

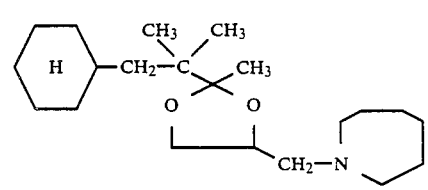

(D)

2-(2-Cyclohexylmethyl)-2-propyl)-2-methyl-4-(1-perhydroazepinylmethyl)-1,3-dioxolane (all known from EP 97,822).

EXAMPLE A

Leptosphaeria nodorum test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to Preparation Examples 3, 4, 5, 6, 7 and 11.

EXAMPLE B

Sphaerotheca test (cucumber) / protective

Solvent: 4.7 parts by weight of acetone
Emulsifier: 0.3 parts by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

To test for protective activity, young plants are sprayed with the preparation of active compound until dripping wet. After the spray coating has dried on, the plants are dusted with conidia of the fungus Sphaerotheca fuliginea.

The plants are then placed in a greenhouse at 23 to 24° C. and at a relative atmospheric humidity of about 75%.

Evaluation is carried out 10 days after the inoculation.

In this test, a clearly superior activity compared with the prior art is shown, for example, by the compounds according to Preparation Example 8.

It is understood that the specification and examples are illustrative but not limitative of the present invention and that other embodiments within the spirit and scope of the invention will suggest themselves to those skilled in the art.

We claim
1. A substituted dioxolanylethylamine of the formula

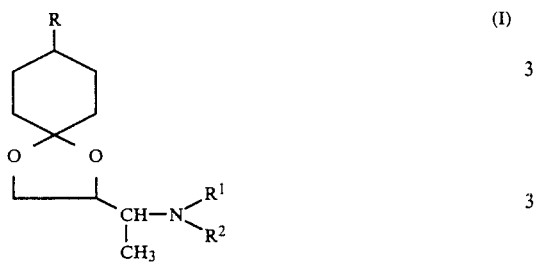

wherein
R represents straight-chain or branched alkyl having 1 to 12 carbon atoms, or represents cycloalkylalkyl or cycloalkyl having in each case 3 to 7 carbon atoms in the cycloalkyl part and if appropriate 1 to 6 carbon atoms in the straight-chain or branched alkyl part and in each case optionally substituted by one or more identical or different substituents from the group consisting of halogen and straight-chain or branched alkyl having 1 to 8 carbon atoms, or represents aralkyl or aryl having in each case 6 to 10 carbon atoms in the aryl part and if appropriate 1 to 6 carbon atoms in the straight-chain or branched alkyl part and in each case optionally substituted by one or more identical or different substituents from the group consisting of halogen and straight-chain or branched alkyl having 1 to 8 carbon atoms, and $R^1$ and $R^2$ independently of one another each represents hydrogen, or represents in each case straight-chain or branched alkyl having 1 to 12 carbon atoms, alkenyl having 3 to 8 carbon atoms, hydroxyalkyl having 2 to 6 carbon atoms, alkoxyalkyl or dialkoxyalkyl having in each case 1 to 6 carbon atoms or hydroxyalkoxyalkyl having 2 to 6 carbon atoms in the individual alkyl parts, or represents alkoxycarbonylalkyl having 1 to 6 carbon atoms per alkoxy and alkyl part, or represents in each case straight-chain or branched dioxolanylalkyl, dioxanylalkyl or oxolanylalkyl having in each case 1 to 4 carbon atoms in the alkyl part, or represents cycloalkyl or cycloalkylalkyl having in each case 3 to 7 carbon atoms in the cycloalkyl part and if appropriate 1 to 4 carbon atoms in the straight-chain or branched alkyl part and in each case optionally substituted in the cycloalkyl part by one or more identical or different substituents selected from the group consisting of halogen, and in each case straight-chain or branched alkyl, alkoxy, halogenoalkyl or halogenoalkoxy having in each case 1 to 4 carbon atoms and if appropriate 1 to 9 identical or different halogen atoms; or furthermore represents arylalkyl, arylalkenyl or aryl having in each case 6 to 10 carbon atoms in the aryl part and if appropriate up to 6 carbon atoms in the straight-chain or branched alkyl or alkenyl part and in each case optionally substituted in the aryl part by one or more identical or different substituents selected from the group consisting of halogen, cyano, nitro and in each case straight-chain or branched alkyl, alkoxy, alkylthio, halogenoalkyl, halogenoalkoxy, halogenoalkylthio, alkoxycarbonyl or alkoximinoalkyl having in each case 1 to 4 carbon atoms in the individual alkyl parts and if appropriate 1 to 9 identical or different halogen atoms, or $R^1$ and $R^2$, together with the nitrogen atom to which they are bonded, represent a saturated 5- to 7-membered heterocyclic radical which can optionally contain a further hetero atom and is optionally substituted by one or more identical or different substituents selected from the group consisting of in each case straight-chain or branched alkyl or hydroxyalkyl having in each case 1 to 4 carbon atoms, or an acid addition salt thereof.

2. A substituted dioxolanylethylamine or salt thereof according to claim 1, wherein
R represents straight-chain or branched alkyl having 1 to 8 carbon atoms, or represents cyclohexyl which is optionally substituted by one to three identical or different substituents from the group consisting of chlorine, methyl, ethyl, n- or i-propyl and n-, i-, s-or t- butyl, or represents cyclohexylalkyl having 1 to 4 carbon atoms in the straight-chain or branched alkyl part and optionally substituted in the cyclohexyl part by one to three identical pr different substituents from the group consisting of chlorine, methyl, ethyl, n-or i-propyl and n-, i-, s- or t-butyl, or represents phenyl which is optionally substituted by one to three identical or different substituents from the group consisting of fluorine, chlorine, bromine, methyl, ethyl, n- or i-propyl, n-, i-, s- or t-butyl, or represents phenylalkyl-having 1 to 4 carbon atoms in the straight-chain or branched alkyl part and optionally substituted in the phenyl part by one to three identical or different substituents from the group consisting of fluorine, chlorine, bromine, methyl, ethyl, n- or i-propyl and n-, i-, s- or t-tutyl, and $R^1$ and $R^2$ independently of one another each represents hydrogen, methyl, ethyl, n- or i-propyl, n-, i-, s- or t-butyl, n- or i-pentyl, n- or i-hexyl, n-or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, methoxycarbonylmethy, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, dioxanylethyl, oxolanylmethyl or oxolanylethyl, or represents cyclopropyl, cyclopropylmethyl, cyclopropylethyl, cyclopropylpropyl, cyclopentyl, cyclopentylmethyl, cyclohexyl or cyclohexylmethyl, in each case optionally substituted by one to five identical or different substituents from the grcuo consisting of fluorine, chlorine, bromine, methyl, ethyl, n- or i-propyl, n-, i-, s- or t-butyl, trifluoromethyland trifluoromethoxy, or represents phenyl, benzyl or phenylethyl in each case optionally substituted by one to three identical or different substituents, selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl and methoximinomethyl, or R¹ and R², together with the nitrogen atom to which they are bonded, represent a heterocyclic radical of the formula

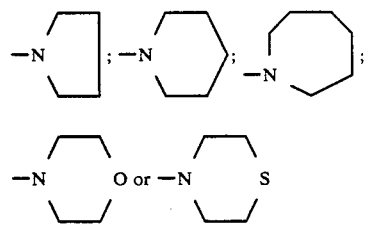

which is optionally substituted by one to three identical or different substituents selected from the group consisting of methyl, ethyl and hydroxymethyl.

3. A substituted dioxolanylethylamine or salt thereof according to claim 1, wherein R represents cyclohexyl or phenyl, or represents one of the radicals

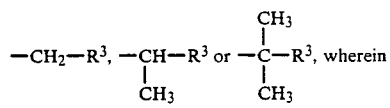

R³ in each case represents hydrogen, methyl, ethyl, n- or i-propyl, n-, i-, s- or t-butyl, neopentyl, cyclohexyl or phenyl, R¹ and R² independently of one another each represents hydrogen, methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, oxanylethyl, dioxanylmethyl, oxolanylmethyl, oxolanylethyl, cyclopropylmethyl, dichlorocyclopropylmethyl, dimethylcyclopropylmethyl, dichlorodimethylcyclopropylmethyl, cyclopentyl, cyclohexyl or cyclohexylmethyl, or cyclopentyl, cyclohexyl or cyclohexylmethyl, or R¹ and R², together with the nitrogen atom to which they are bonded, represent one of the heterocyclic radicals

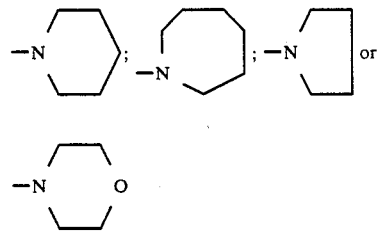

which is optionally substituted by one to three identical or different substituents selected from the group consisting of methyl, ethyl and hydroxymethyl.

4. A compound according to claim 1, wherein such compound is 8-t- butyl-2-[1-piperidyl)-ethyl]-1,4-dioxaspiro [4,5]decane of the formula

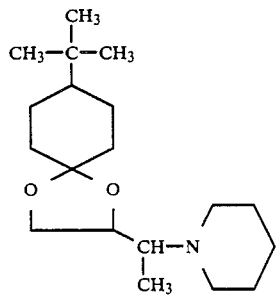

or an acid addition salt thereof.

5. A compound according to claim 1, wherein such compound is 8-t-butyl-2-[1-(4-methylcyclohexylamino)-ethyl]-1,4-dioxaspiro[4,5]decane of the formula

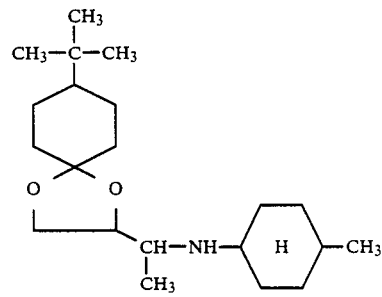

or an acid addition salt thereof.

6. A compound according to claim 1, wherein such compound is 8-t-butyl-2-[1-(cyclohexylmethylamino)-ethyl]-1,4-dioxaspiro[4,5]decane of the formula

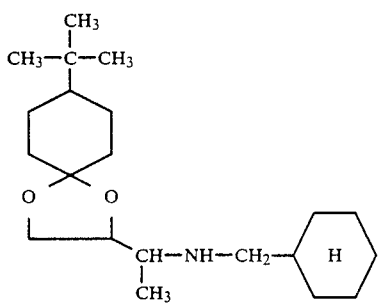

or an aicd addition salt thereof.

7. A compound according to claim 1, wherein such compound is 8-t-butyl-2-[1-(cyclohexylmethylamino)-ethyl]-1,4-dioxaspiro[4,5]decane of the formula

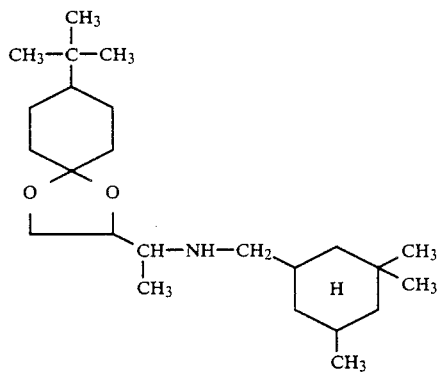

or an acid addition salt thereof.

8. A fungicidal composition comprising a fungicidally effective amount of a compound or salt according to claim 1 and a diluent.

9. A method of combating fungi which comprises applying to said fungi or to a fungus habitat a fungicidally effective amount of a compound or salt according to claim 1.

10. The method according to claim 9, wherein such compound is 8-t-butyl-2-[1-piperidyl)-ethyl]-1,4-dioxaspiro[4,5]decane, 8-t-butyl-2-[1-(4-methylcyclohexylamino)-ethyl]-1,4-dioxaspiro[4,5]decane, 8-t-butyl-2-[1-(cyclohexylmethylamino)-ethyl]-1,4-dioxaspiro[4,5]decane or 8-t-butyl-2-[1-(3,3,5-trimethylcyclohexylmethylamino)-ethyl]-1,4-dioxaspiro[4,5]decane or an acid addition salt thereof.

11. A substituted dioxolane of the formula

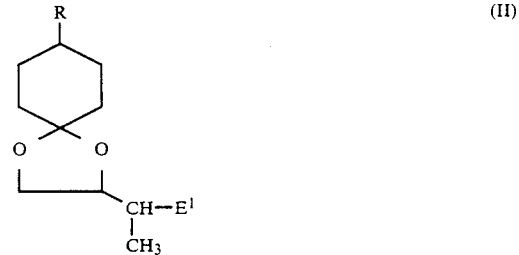

in which
R represents straight-chain or branched alkyl having 1 to 12 carbon atoms, or represents cycloalkylalkyl or cycloalkyl having in each case 3 to 7 carbon atoms in the cycloalkyl part and if appropriate 1 to 6 carbon atoms in the straight-chain or branched alkyl part and in each case optionally substituted by one or more identical or different substituents by one or more identical or different substituents from the group consisting of halogen and straight-chain or branched alkyl having 1 to 8 carbon atoms, or represents aralkyl or aryl having in each case 6 to 10 carbon atoms in the aryl part and if appropriate 1 to 6 carbon atom sin the straight-chain or branched alkyl part and in each case optionally substituted by one or more identical or different substituents from the group consisting of halogen and straight-chain or branched alkyl having 1 to 8 carbon atoms, and $E^1$ represents an electron-withdrawing leaving group.

* * * * *

UNITED STATES PATENT AND TRADEMARK OFFICE
CERTIFICATE OF CORRECTION

PATENT NO. : 4,985,421

DATED : January 15, 1991

INVENTOR(S) : Kramer et al.

It is certified that error appears in the above-identified patent and that said Letters Patent is hereby corrected as shown below:

Col. 23, claim 7 line 2     After " 1-( " insert -- 3,3,5-trimethyl --

Col. 24, lines 30-31     Delete " by one or more identical or different substituents "

Signed and Sealed this

Twentieth Day of April, 1993

Attest:

MICHAEL K. KIRK

Attesting Officer     Acting Commissioner of Patents and Trademarks